United States Patent [19]

Partenheimer et al.

[11] Patent Number: 5,194,633
[45] Date of Patent: Mar. 16, 1993

[54] PREPARATION OF 1,1,1,3,3,3-HEXAFLUORO-2,2-DI(3,4-DICARBOXYPHENYL)PROPANE ANHYDRIDE

[75] Inventors: Walter Partenheimer; Douglas E. Fjare, both of Naperville; Gayle G. Chany, Bolingbrook, all of Ill.

[73] Assignee: Amoco Corporation, Chicago, Ill.

[21] Appl. No.: 798,171

[22] Filed: Nov. 26, 1991

Related U.S. Application Data

[63] Continuation of Ser. No. 530,642, May 30, 1990, abandoned.

[51] Int. Cl.$^5$ ............................................. C07D 307/77
[52] U.S. Cl. ..................................................... 549/241
[58] Field of Search ........................................ 549/241

[56] References Cited

U.S. PATENT DOCUMENTS 4,863,640  9/1989  Scola .................................... 549/241
4,885,116 12/1989  Alston et al. ......................... 549/241
4,987,238  1/1991  Röhischeid ........................... 549/241
5,004,797  4/1991  Röhrscheid et al. ................ 549/241

Primary Examiner—Cecilia Tsang
Attorney, Agent, or Firm—Thomas E. Nemo; Wallace L. Oliver; Frank J. Sroka

[57] ABSTRACT

A process for preparing 1,1,1,3,3,3-hexafluoro-2,2-di(3,4-dicarboxyphenyl) propane anhydride is disclosed. 1,1,1,3,3,3-hexafluoro-2,2-di(3,4-dimethylphenyl) propane is oxidized under liquid phase conditions in the presence of an oxygen-containing gas, bromine and heavy metal catalyst components to 1,1,1,3,3,3-hexafluoro-2,2-di(3,4-dicarboxyphenyl) propane in high yield. Addition of an anhydride of a low molecular weight carboxylic acid to the oxidation reaction mixture converts the 1,1,1-hexafluoro-2,2-di(3,4-dicarboxyphenyl)propane to 1,1,1,3,3,3-hexafluoro-2,2-di(3,4-dicarboxyphenyl) propane anhydride.

7 Claims, No Drawings

PREPARATION OF 1,1,1,3,3,3-HEXAFLUORO-2,2-DI(3,4-DICARBOXY-PHENYL)PROPANE ANHYDRIDE

This is a continuation of application Ser. No. 07/530,642, filed May 30, 1990 now abandoned.

FIELD OF THE INVENTION

This invention relates to the preparation of 1,1,1,3,3,3-hexafluoro-2,2-di(3,4-dicarboxyphenyl) propane anhydride.

BACKGROUND OF THE INVENTION 1,1,1,3,3,3-Hexafluoro-2,2-di(3,4-dicarboxyphenyl) propane anhydride also known as 4,4'-(hexafluoroisopropylidene)-bis(phthalic anhydride) and hereinafter referred to as 6-FDA is a useful chemical intermediate. Polyimides made from 6-FDA have desirable properties such as low dielectric constants, low moisture uptake and the proper thermal stability making them useful as coatings and dielectrics in electronic applications. Other potential uses for polymers made with 6-FDA are composites, molded parts and optical fibers.

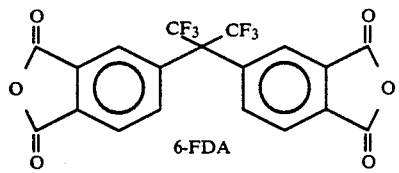

Oxidation processes for producing 6-FDA from 1,1,1,3,3,3-hexafluoro-2,2-di(3,4-dimethylphenyl) propane, also known as 4,4'-(hexafluoroisopropylidene)-bis(o-xylene) and herein after referred to as 6-FXP, are described in Coe, U.S. Pat. No. 3,310,573 where 6-FXP is first oxidized using potassium permanganate in a solvent of pyridine and water to the tetracarboxylic acid, 1,1,1,3,3,3-hexafluoro-2,2-di(3,4-dicarboxyphenyl) propane, also known as 4,4'-(hexafluoroisopropylidene)-bis(phthalic acid) and hereinafter referred to as 6-FTA. The tetracarboxylic acid, 6-FTA, is then dehydrated in a separate step to form 6-FDA.

Another route to 6-FDA from 6-FXP is to utilize the known, so-called, Mid-Century Oxidation process to oxidize 6-FXP to the tetracarboxylic acid, 6-FTA. In this process the 6-FXP is oxidized to 6-FTA in the liquid phase using air or other suitable source of molecular oxygen and an oxidation catalyst comprising heavy metal components and a bromine source. Such a suitable liquid phase oxidation process is described in Saffer and Barker, U.S. Pat. No. 2,833,816. This catalytic, liquid phase oxidation reaction converts the methyl substituents on the 6-FXP molecule to carboxylic acid substituents.

In the Mid-Century-type oxidation process when used to prepare an aromatic carboxylic acid such as terephthalic acid by the oxidation of p-xylene, the terephthalic acid product is substantially insoluble in the oxidation reaction mixture or reaction product mixture and precipitates rapidly from these mixtures. This is particularly the case after the reaction product mixture is cooled to below the temperature used for the oxidation. Generally, the oxidation reaction solvent is a low molecular weight aliphatic carboxylic acid such as acetic acid. Consequently, the product aromatic carboxylic acid, such as terephthalic acid, is easily recoverable by simply separating the insoluble aromatic acid product from the oxidation reaction product mixture.

Similarly, the liquid phase, heavy-metal catalyzed oxidation of 6-FXP to the tetracarboxylic acid, 6-FTA proceeds in high yield and is an efficient method for preparing 6-FTA. However, the 6-FTA is generally soluble in the oxidation reaction product mixture and does not precipitate at all or only very slowly and cannot therefore be easily recovered from the reaction mixture to be converted into the desired dianhydride, 6-FDA.

A new process for converting 6-FXP to 6-FDA utilizing the Mid-Century-type liquid phase oxidation process and providing for the rapid and economical recovery of 6-FDA would be highly advantageous. The present invention provides such a process.

SUMMARY OF THE INVENTION 1,1,1,3,3,3-Hexafluoro-2,2-di(3,4-dimethylphenyl) propane (6-FXP) is oxidized to 1,1,1,3,3,3-hexafluoro-2,2-di(3,4-dicarboxyphenyl) propane (6-FTA) in relatively high yields by a known liquid phase oxidation process using heavy metal catalyst components, a source of bromine and air or other suitable sources of molecular oxygen. The solvent for the oxidation reaction is a low molecular weight aliphatic carboxylic acid and the catalyst comprises cobalt and manganese components.

More specifically, the presently contemplated process for preparing 6-FDA by the liquid phase oxidation of 6-FXP comprises introducing into an oxidation reactor a mixture comprising 6-FXP, an oxidation solvent comprising an aliphatic acid having 2 to 6 carbon atoms per molecule, an oxygen-containing gas and an oxidation catalyst comprising cobalt, manganese and bromine components; maintaining said mixture at a reaction temperature in the range of about 100° F. to about 500° F., at a reaction pressure sufficient to maintain at least a portion of said mixture in the liquid phase, and for a time sufficient to oxidize at least a portion of the 6-FXP and form a first product mixture comprising 6-FTA; forming a second product mixture comprising 6-FDA by treating said first product mixture with an amount of aliphatic anhydride sufficient to convert at least a portion of said 6-FTA to 6-FDA, said aliphatic anhydride having 4 to 12 carbon atoms per molecule; precipitating said 6-FDA from said second product mixture; recovering precipitated 6-FDA.

A surprising and unexpected feature of the present process is that the addition of a low molecular weight aliphatic anhydride, such as acetic anhydride, to the product mixture after the oxidation of 6-FXP to 6-FTA converts the soluble 6-FTA to the desired 6-FDA. Surprisingly, the 6-FDA is insoluble in the oxidation reaction product mixture containing the oxidation solvent and the 6-FDA rapidly precipitates from the oxidation reaction product mixture. Recovery of the precipitated 6-FDA is possible by any one of a number of separation methods including simple filtration or centrifugation.

Further other features and embodiments and the like of this invention will become apparent to those skilled in the art from the present description of this invention.

DETAILED DESCRIPTION OF THE PREFERRED EMBODIMENTS

According to the process of the present invention, 6-FXP is heated in a reaction zone under liquid phase conditions in the presence of an oxidation catalyst comprising cobalt, manganese and bromine components, an oxidation solvent containing at least one aliphatic carboxylic acid having 2 to 6 carbon atoms per molecule and an oxygen-containing gas such as an air or oxygen. The mixture is heated or maintained at a reaction temperature sufficient to effect the reaction comprising the oxidation of the methyl substituents on the 6-FXP molecule to carboxylic acid substituents. The reaction pressure of the oxidation reaction is sufficient to maintain at least a portion, and preferably at least 70% (by volume), of the reaction mixture in the liquid phase. More preferably, the reaction pressure is in the range of about 0.1 atmospheres to about 100 atmospheres, and most preferably in the range of 1.0 to about 50 atmospheres. The reaction temperature may range throughout the course of the oxidation reaction for converting 6-FXP to 6-FTA. Preferably the reaction temperature is in the range of about 100° F. to about 500° F., and more preferably in the range of about 250° F. to about 450° F. Any suitable means for controlling the oxidation reaction temperature including external heating and cooling means are suitable. A means for cooling refluxing reaction solvent is a preferred method for controlling the temperature of the generally exothermic oxidation reaction.

The oxygen-containing gas is preferably air. Mixtures of oxygen and an inert gas, or mixture of inert gases, are also suitable. The oxygen content of the oxygen-containing gas can range from about 0.1% to 100% molecular oxygen. Preferably the oxygen-containing gas is introduced into the oxidation reaction mixture during the course of the oxidation reaction in an amount sufficient to supply the reaction mixture with enough oxygen to maintain the oxidation reaction at a reasonable rate, and preferably in an amount at least sufficient to maintain a molar excess of oxygen relative to the 6-FXP present.

The oxidation solvent comprises one or more low molecular weight aliphatic carboxylic acids having 2 to 6 carbon atoms per molecule. Acetic acid and propionic acid are suitable. Acetic acid is the preferred solvent. The low molecular weight carboxylic acid oxidation solvent may also contain low levels of water. Suitable acetic acid contains about 0.1 to about 10 wt. % water. The weight ratio of low molecular weight carboxylic acid oxidation solvent to the 6-FXP feed material in the reaction mixture is preferably in the range of about 15:1 about 0.2:1, more preferably in the range of about 5:1 to about 1:1.

The oxidation catalyst employed in the process of this invention preferably comprises cobalt, manganese and bromine components and can additionally contain other metal components such as zirconium. More preferably the catalyst consists essentially of cobalt, manganese and bromine components, or cobalt, manganese, zirconium and bromine components. Each of the cobalt and manganese or cobalt, manganese and zirconium components can be used in each of its known ionic or combined forms that provide soluble forms of cobalt and manganese or cobalt, manganese and zirconium in the solvent used for the oxidation reaction. For example, and without intending to limit the possible types of compounds, cobalt, manganese and zirconium carbonates, acetates and bromides in either their anhydrous or hydrated forms are suitable.

The bromine component for the process of this invention can be molecular bromine, ionic forms of bromine such as hydrogen bromide, sodium bromide, potassium bromide, ammonium bromide, etc., or organic bromides which produce bromide ions at the operating temperature of the oxidation reaction, such as benzylbromide, mono- and di-bromoacetic acid, ethylene dibromide, dibromoethane, tetrabromoethane, etc.

Preferably, the weight ratio of cobalt (calculated as elemental cobalt) in the cobalt component of the oxidation catalyst-to-6-FXP in the oxidation reaction mixture is in the range of about 0.1 to about 50 milligram atoms (mga) per gram mole of 6-FXP, the weight ratio of manganese (calculated as elemental manganese) in the manganese component of the oxidation catalyst-to-cobalt (calculated as elemental cobalt) in the cobalt component of the oxidation catalyst in the reaction mixture is in the range of about 0.1 to about 50 mga per mga of cobalt and, the weight ratio of bromine (calculated as elemental bromine) in the bromine component of the catalyst-to-total cobalt and manganese (calculated as elemental cobalt and elemental manganese) in the cobalt and manganese components of the catalyst in the oxidation reaction mixture is in the range of about 0.1 to about 4.0 mga per mga of total cobalt and manganese. The total bromine in molecular bromine or ionic bromide is used to determine the elemental bromine-to-total cobalt and manganese milligram atom ratio of 0.1:1.0 to 4.0:1.0.

The process of this invention can be performed in either a batch, semi-continuous or continuous manner. By batch it is meant that all of the components of the reaction mixture are charged initially all at once. By semi-continuous, at least a portion of one or more of the reaction mixture components is charged during the course of the oxidation reaction. By continuous it is meant that the reactants are continuously charged to the reaction mixture and a product containing stream is continuously removed from the reaction mixture or reaction zone where the oxidation reaction is occurring.

At the completion of the oxidation reaction a portion or all of the 6-FXP is oxidized to the tetracarboxylic acid, 6-FTA. The 6-FTA is generally soluble in the oxidation reaction product mixture, also referred to as the Total Reactor Effluent or TRE, formed by the oxidation reaction. This product mixture also contains the oxidation solvent, reaction intermediates and side-products, water that may have been initially charged with the reaction solvent and water formed by the oxidation reaction, catalyst metals and bromine containing components.

According to the process of this invention the oxidation reaction product mixture containing 6-FTA is treated with a quantity of an anhydride of a low-molecular weight aliphatic carboxylic acid sufficient to convert the 6-FTA to 6-FDA. The 6-FDA rapidly precipitates from the oxidation product mixture and is readily recovered.

Prior to the addition of the anhydride, the oxidation reaction product mixture may be reduced in volume, preferably by 25 to 75% of the original volume, by any one of a number of techniques as, for example, heating at atmospheric or reduced pressure to boil-off volatile components. The product mixture may be sparged with air or other gas while applying heat to accelerate evaporation of volatile components, at atmospheric or at reduced pressure. Evaporation of the volatile components at ambient conditions, although time consuming, is also possible. Additionally, the product mixture may be reduced in volume by the methods mentioned above subsequent to the addition of the aliphatic anhydride. Anhydride addition to the product mixture can be done when the product mixture is still at the oxidation reaction temperature, or at a suitable lower or still higher temperature. Preferably, the product mixture is at ambient or near ambient temperature. Preferably, the anhydride used to convert the 6-FTA to 6-FDA contains 4 to 12 carbon atoms per anhydride molecule. Acetic anhydride and propionic anhydride are particularly preferred anhydrides. Acetic anhydride is the most preferred anhydride, particularly when acetic acid is used as the solvent for the oxidation reaction.

The amount of anhydride added to the product mixture from the oxidation reaction is an amount sufficient to convert at least a portion of the 6-FTA to 6-FDA, preferably an amount to convert most of the 6-FTA to 6-FDA. Most preferably, the amount of anhydride added should be an amount that will cause the precipitation of most or substantially all of the 6-FDA from the oxidation reaction product mixture and preferably within a short period of time, generally within about an hour and preferably within about fifteen minutes, after the addition of the anhydride. If precipitation of the 6-FDA from the product reaction mixture fails to occur within a short period of time after the addition of the anhydride, the product mixture can be reduced in volume by one or more of the methods described above, or by some equivalent method, and/or cooled to promote precipitation of the 6-FDA from the product reaction mixture. Stirring promotes the precipitation of the 6-FDA. In summary, 6-FTA is generally soluble in the oxidation reaction product mixture and the addition of anhydrides of low molecular weight carboxylic acids readily converts the soluble 6-FTA to insoluble 6-FDA which rapidly precipitates from the oxidation reaction product mixture.

Precipitated 6-FDA can be separated from the oxidation reaction product mixture by any one of a number of methods. Filtration, either by gravity or aided by application of pressure or use of a vacuum, is a suitable method. Centrifugation of the solid, insoluble 6-FDA, from the rest of the product mixture is also a suitable method. Equivalent methods, such as using a cyclone separator, are also suitable.

The 6-FDA recovered from the oxidation product mixture after the addition of an anhydride may contain various levels of impurities and other undesired components as, for example, residual amounts of catalyst metals. Purification can be achieved by recrystallizing the 6-FDA with or without the use of adsorbents such as activated carbon. A particularly effective method for purifying 6-FDA produced by the process of this invention comprises the recrystallization of 6-FDA from a solvent mixture comprising one or more aliphatic anhydrides and one or more low molecular weight aliphatic carboxylic acids. The recrystallization process comprises dissolving the 6-FDA in the solvent mixture of anhydride and low molecular weight aliphatic carboxylic acid while heating the mixture. Preferably the anhydride is the anhydride of the low molecular weight carboxylic acid wherein the low-molecular weight carboxylic acid contains 2 to 6 carbon atoms per molecule. Acetic acid and acetic anhydride are the most preferred components of the recrystallization solvent. The ratio of low molecular weight carboxylic acid to anhydride in the recrystallization solvent may range from about 100:1 to about 0.1:1 by weight. Preferably from about 10:1 to about 1:1 by weight. The amount of the mixture of anhydride and low-molecular weight carboxylic acid required to recrystallize the 6-FDA will depend on the purity of the 6-FDA desired and on the temperature to which the mixture is heated for dissolving 6-FDA. Higher temperatures are possible if pressures greater than atmospheric pressure are used. Generally, the amount of mixture of anhydride and low-molecular weight carboxylic acid should be at least the minimum amount required to dissolve the 6-FDA at the boiling (refluxing) temperature of the mixture. Upon cooling, purified 6-FDA precipitates and can be recovered by any one of a number of methods such as filtration or centrifugation. When the 6-FDA is dissolved in the mixture of anhydride and low molecular weight carboxylic acid treatment with an activated carbon or other adsorbent further aids purification of the 6-FDA.

6-FDA that precipitates from the oxidation reaction mixture after the addition of the aliphatic anhydride and 6-FDA that precipitates from the recrystallization solvent mixture may be in the form of a di-solvate. For example, when acetic acid is used as the oxidation reaction solvent or solvent for recrystallizing 6-FDA, the 6-FDA precipitates as a complex comprising one 6-FDA molecule and two molecules of acetic acid. The acetic acid or other low molecular weight carboxylic acid may be removed from the 6-FDA by heating the 6-FDA complex at a temperature and for a time sufficient to remove the low molecular weight carboxylic acid. Preferably, the temperature required to remove the complexed low molecular weight carboxylic acid is at least 200° F., and more preferably at least 250° F.

Suitable 6-FXP, the feedstock for the oxidation process of this invention, may be prepared by the method described in U.S. Pat. No. 3,310,573. It is also available from Riedel de Haen AG (West Germany). At times the initial purity of 6-FXP is rather low and it may be purified prior to oxidation. If desired, the 6-FXP can be purified by recrystallization from either acetic acid (5% water), hexane or ethanol. Some of the impurities in the 6-FXP are the trimethyl- and pentamethyl-1,1,1,3,3,3-hexafluoro-2,2-diphenyl propane compounds as well as isomeric tetramethyl- compounds. Related compounds with only one trifluoromethyl group are also impurities. Recrystallization from ethanol produced the greatest increase in purity. Even without recrystallization of the 6-FXP feedstock, the oxidation process of this invention and the process of preparing and isolating 6-FDA proceed in high yield. 6-FXP of at least about 80% purity is suitable for the process of this invention. When highly pure 6-FXP is used in the process of this invention, the oxidation reaction product mixture slowly precipitates 6-FXT. This precipitation does not start until about one hour after the oxidation reaction mixture is cooled to ambient temperature.

The following examples are offered to illustrate the present invention but are not intended to limit the scope thereof.

EXAMPLE I

A one-liter, stirred titanium-clad pressure reactor was charged with 500 grams of acetic acid and 36.6 grams (0.0935 moles after correction for purity) of 1,1,1,3,3,3-hexafluoro-2,2-di(3,4-dimethylphenyl)propane (6-FXP). The following catalyst components were also charged to the pressure reactor:

| | |
|---|---|
| cobalt acetate (tetrahydrate) | 2.00 grams |

-continued

| | |
|---|---|
| manganese acetate (tetrahydrate) | 2.00 grams |
| zirconium oxide acetate (hydrate) | 0.398 grams |
| hydrogen bromide | 2.75 grams of a 48 wt. % solution of HBr in water |

The reactor was pressurized with air to 400 psig and heated to 372° F. Air was introduced at a rate of 0.34 ft³/minute during the course of the 20 minute oxidation reaction. During this time period the temperature ranged from 370° to 403° F.

At the end of the reaction, liquid chromatographic analysis of a small sample of the total reactor effluent (TRE) indicated that 1,1,1,3,3,3-hexafluoro-2,2-di(3,4-dicarboxyphenyl)propane (6-FTA) was formed. The total reactor effluent remained liquid after cooling with no precipitation of the tetracarboxylic acid, 6-FTA.

The liquid TRE was reduced in volume to approximately one-half the original volume by evaporation at room temperature. The resulting liquid was divided into a portion weighing approximately 88 grams (the 88 grams portion) and a portion weighing approximately 131 grams (the 131 gram portion). Evaporation of volatile materials in the 88 gram portion resulted in the formation of an oil. Treatment of the oil with acetone or a mixture of acetone and water failed to produce a filterable precipitate. Addition of hexane to the acetone/water solution also failed to produce a precipitate. The 131 gram portion was reduced in volume by drying to 73.4 grams whereupon 18 grams of acetic anhydride were added. After a few minutes of stirring, a large amount of precipitate formed. The mixture was again heated and the precipitate dissolved and did not precipitate upon cooling. Adding 25 grams of acetic anhydride produced, after filtering and drying, 13.7 grams of 91% (wt. %) pure 1,1,1,3,3,3-hexafluoro-2,2-di(3,4-dicarboxyphenyl)propane anhydride (6-FDA). This product also contained <0.23 wt. % 6-FXP. The filtrate, weighing 35.4 grams contained 1.3 grams of 6-FDA. Analysis of the 6-FDA indicated that bromine, cobalt and manganese were present at 580, 660 and 620 parts per million, respectively.

A 11.5 gram sample of the 6-FDA prepared above was dissolved in approximately 70 ml of a 3:1 mixture of acetic acid and acetic anhydride that was previously heated to eliminate water present. Nuchar SA-20 ® activated carbon (0.35 g) and Celite ®, a filtering agent, (0.35 g) were added to the boiling solvent. After boiling for approximately 30 minutes the mixture was filtered and upon cooling the filtrate produced 7.6 grams of 99.5% pure 6-FDA (measured by liquid chromatography) containing less than 0.2 6-FXP. The bromine, cobalt and manganese levels of the 6-FDA were 77, 21 and 3 parts per million, respectively.

This Example shows that 6-FXP can be oxidized to the tetraacid, 6-FTA in high yield using liquid phase air oxidation catalyzed by heavy metals. This Example also demonstrates that 6-FTA does not precipitate from the total reactor effluent and that ordinary procedures were unsuccessful for isolating a solid product. This Example demonstrates that the use of acetic anhydride converts the 6-FTA to 6-FDA and that the 6-FDA is not soluble in the TRE, permitting the easy recovery of 6-FDA. This Example also demonstrates that the 6-FDA can be purified by recrystallization from a mixture of acetic anhydride and acetic acid.

EXAMPLE II

The same reactor as in Example I was charged with 500 grams acetic acid and 200 grams of 83% pure 6-FXP. The following catalyst components were also charged to the reactor:

| | |
|---|---|
| cobalt acetate (tetrahydrate) | 2.00 grams |
| manganese acetate (tetrahydrate) | 2.00 grams |
| hydrogen bromide | 2.79 grams of a 48 wt. % solution of HBr in water |

The reactor was pressurized with air to 170 psig and heated to 335° F. Air was introduced at a rate of 0.60 ft³/minute for the first 30 minutes of the reaction and then at 0.34 ft³/minute for the remaining 15 minutes of the reaction. At approximately 36 minutes into the run the pressure was increased to 270 psig. The reaction temperature ranged from 335° to 383° F.

The TRE remained liquid and without precipitation of 6-FTA even after 24 hours. Addition of 390 ml of acetic anhydride produced a precipitate after about 10 to 15 minutes of stirring.

The solid 6-FDA precipitate was collected by filtration and weighed 162.3 grams. Addition of 50 ml of acetic anhydride to the filtrate produced an additional 18.0 grams of 6-FDA that was recovered by filtration. The 6-FDA was dissolved in 950 ml of a 3:1 (wt) mixture of boiling acetic acid and acetic anhydride. Nuchar SA-20 ® (5.1 g) and Celite ® (5.5 g) were added and the mixture filtered through a bed of Celite ®. After cooling to room temperature the precipitated solids were separated from the recrystallization solvent and heated in a vacuum oven at 240°-250° F. The resulting solid 6-FDA weighed 142.2 grams corresponding to a 69% yield of 6-FDA based on 6-FXP.

EXAMPLE III

The same reactor as in Example I was charged with 500 grams acetic acid and 200.00 grams of 83% pure 6-FXP. The following catalyst components were also charged to the reactor:

| | |
|---|---|
| cobalt acetate (tetrahydrate) | 2.00 grams |
| manganese acetate (tetrahydrate) | 2.00 grams |
| hydrogen bromide | 2.74 grams of a 48 wt. % solution of HBr in water |

The reactor was pressurized with air to 170 psig and heated to 338° F. Air was introduced at a rate of 0.60 ft³/minute for the first 30 minutes of the reaction and at 0.34 ft³/minute for the remaining 20 minutes of the reaction. The pressure was increased to 200 psig after 8 minutes and to 270 psig after 35 minutes. The temperature of the reaction mixture ranged from 338° to 386° F.

The TRE remained liquid and without precipitation of 6-FTA after more than 24 hours as in Example II. Addition of 400 ml of acetic anhydride, however, produced a precipitate of 6-FDA after about 5 to 10 minutes of stirring. The 6-FDA recovered by filtration weighed 255.6 grams. This sample was characterized as the di-acetic acid solvate of 6-FDA by infrared spectroscopic analysis, and by elemental carbon and hydrogen analysis.

EXAMPLE IV

A reaction was run similarly to that of Example III except the catalyst components were as follows:

| | |
|---|---|
| cobalt acetate (tetrahydrate) | 1.00 grams |
| manganese acetate (tetrahydrate) | 1.00 grams |
| hydrogen bromide | 1.40 grams of a 48 wt. % solution of HBr in water |

After the addition of 400 ml acetic anhydride to the TRE and the addition of 25 ml of acetic anhydride to the filtrate, the 6-FDA di-acetic acid solvate recovered by filtration weighed 223.6 g.

Examples II, III and IV demonstrate that 6-FXP can be oxidized using cobalt, manganese and bromine catalyst components to produce 6-FDA in high yield. Example IV demonstrates that the use of lower amounts of catalyst components decreases the yield somewhat under otherwise similar reaction conditions. Examples II, III and IV all demonstrate that the addition of acetic anhydride to the total reactor effluent caused the rapid precipitation of 6-FDA, the desired anhydride product and permitted easy recovery of the 6-FDA.

That which is claimed is:

1. A process for preparing 1,1,1,3,3,3-hexafluoro-2,2-di(3,4-dicarboxyphenyl) propane anhydride (6-FDA) by the liquid phase oxidation of 1,1,1,3,3,3-hexafluoro-2,2-di(3,4-dimethylphenyl) propane (6-FXP), which process comprises:
   (a) introducing into an oxidation reactor a mixture comprising 6-FXP, an oxidation solvent comprising an aliphatic acid having 2 to 6 carbon atoms per molecule, an oxygen-containing gas, and an oxidation catalyst comprising cobalt, manganese and bromine components;
   (b) maintaining said mixture at a reaction temperature in the range of about 100° F. to about 500° F., at a reaction pressure sufficient to maintain at least a portion of said mixture in the liquid phase, and for a time sufficient to oxidize at least a portion of the 6-FXP and form a first product mixture comprising 1,1,1,3,3,3-hexafluoro-2,2-di(3,4-dicarboxyphenyl) propane (6-FTA);
   (c) forming a second product mixture comprising 6-FDA by treating said first product mixture with an amount of aliphatic anhydride sufficient to convert at least a portion of said 6-FTA to 6-FDA, said aliphatic anhydride having 4 to 12 carbon atoms per molecule;
   (d) precipitating said 6-FDA from said second product mixture;
   (e) recovering precipitated 6-FDA; and
   (f) heating recovered precipitated 6-FDA to remove aliphatic carboxylic acid.

2. The process of claim 1 wherein weight ratio of cobalt in the cobalt component of the oxidation catalyst-to-6-FXP in the mixture is in the range of about 0.1 to about 50 milligram atoms (mga) per gram mole of 6-FXP, weight ratio of manganese in the manganese component of the oxidation catalyst-to-cobalt in the cobalt component of the oxidation catalyst is in the range of about 0.1 to about 50 mga per mag of cobalt, and weight ratio of bromine in the bromine component of the catalyst-to-total cobalt and manganese in the cobalt and manganese components of the oxidation catalyst is in the range of about 0.1 to about 4.0 mga per mga of total cobalt and manganese.

3. The process of claim 2 wherein said aliphatic acid is acetic acid and said oxygen-containing gas is air.

4. The process of claim 1 wherein said amount of aliphatic anhydride is an amount sufficient to precipitate said 6-FDA from said second product mixture.

5. The process of claim 4 wherein said aliphatic anhydride is acetic anhydride.

6. The process of claim 1 wherein said precipitated 6-FDA is purified by recrystallizing said precipitated 6-FDA in a mixture of acetic anhydride and acetic acid.

7. The process of claim 1 wherein said precipitated 6-FDA is heated at a temperature and for a time sufficient to remove complexed low molecular weight carboxylic acid.

* * * * *